(12) United States Patent
Snyder et al.

(10) Patent No.: US 9,861,352 B2
(45) Date of Patent: Jan. 9, 2018

(54) METHOD AND APPARATUS FOR ATTACHING AN ELONGATED OBJECT TO BONE

(71) Applicant: Redyns Medical LLC, Los Angeles, CA (US)

(72) Inventors: Nathan B. Snyder, Los Angeles, CA (US); Stephen J. Snyder, Encino, CA (US); Ronald Litke, Sandy Hook, CT (US)

(73) Assignee: Redyns Medical LLC, Los Angeles, CA (US)

( * ) Notice: Subject to any disclaimer, the term of this patent is extended or adjusted under 35 U.S.C. 154(b) by 0 days.

(21) Appl. No.: 14/817,267

(22) Filed: Aug. 4, 2015

(65) Prior Publication Data

US 2016/0030033 A1 Feb. 4, 2016

Related U.S. Application Data

(63) Continuation of application No. 13/370,138, filed on Feb. 9, 2012, now Pat. No. 9,095,332.

(60) Provisional application No. 61/441,121, filed on Feb. 9, 2011.

(51) Int. Cl.
*A61B 17/60* (2006.01)
*A61B 17/04* (2006.01)

(52) U.S. Cl.
CPC ...... *A61B 17/0401* (2013.01); *A61B 17/0483* (2013.01); *A61B 2017/0409* (2013.01)

(58) Field of Classification Search
CPC ............ A61B 17/8869; A61B 17/7037; A61B 17/7041; A61B 17/7032; A61B 17/8861; A61B 17/7004; A61B 17/842; A61B 17/848; A61B 17/66; A61B 17/8897; A61B 2019/307; A61B 2017/0409; A61B 2019/464
USPC .......................... 606/62–68, 96–98, 102–104
See application file for complete search history.

(56) References Cited

U.S. PATENT DOCUMENTS

| 5,139,500 | A | * | 8/1992 | Schwartz ........... A61B 17/1697 606/103 |
| 5,266,075 | A | | 11/1993 | Clark et al. |
| 5,370,647 | A | | 12/1994 | Graber et al. |
| 5,431,651 | A | * | 7/1995 | Goble ................ A61B 17/1714 606/102 |
| 5,601,562 | A | | 2/1997 | Wolf et al. |
| 5,609,595 | A | | 3/1997 | Pennig |
| 7,341,592 | B1 | | 3/2008 | Walters et al. |
| 8,002,778 | B1 | * | 8/2011 | Meridew ............... A61F 2/0805 606/104 |
| 2004/0087953 | A1 | | 5/2004 | Singhatat et al. |
| 2004/0092936 | A1 | | 5/2004 | Miller et al. |

(Continued)

*Primary Examiner* — Eduardo C Robert
*Assistant Examiner* — Tara R Carter
(74) *Attorney, Agent, or Firm* — Pandiscio & Pandiscio

(57) ABSTRACT

A method for attaching an elongated object to bone, the method comprising:
  forming a hole in the bone;
  positioning a loop of the elongated object in the hole;
  advancing a surgical wire into the bone so that the surgical wire is directed toward a location within the interior of the loop; and
  severing the surgical wire intermediate its length so as to create a distal portion and a remainder portion and, if the distal portion of the surgical wire does not extend through the loop, further advancing the distal portion of the surgical wire so that it extends through the loop.

19 Claims, 21 Drawing Sheets

(56) References Cited

U.S. PATENT DOCUMENTS

| | | |
|---|---|---|
| 2005/0070899 A1* | 3/2005 | Doubler ............ A61B 17/8869 606/264 |
| 2007/0167950 A1 | 7/2007 | Tauro et al. |
| 2008/0312693 A1 | 12/2008 | Trautwein et al. |
| 2009/0088798 A1 | 4/2009 | Snyder et al. |
| 2009/0287225 A1 | 11/2009 | Olsen et al. |
| 2010/0312249 A1 | 12/2010 | Sanders |

* cited by examiner

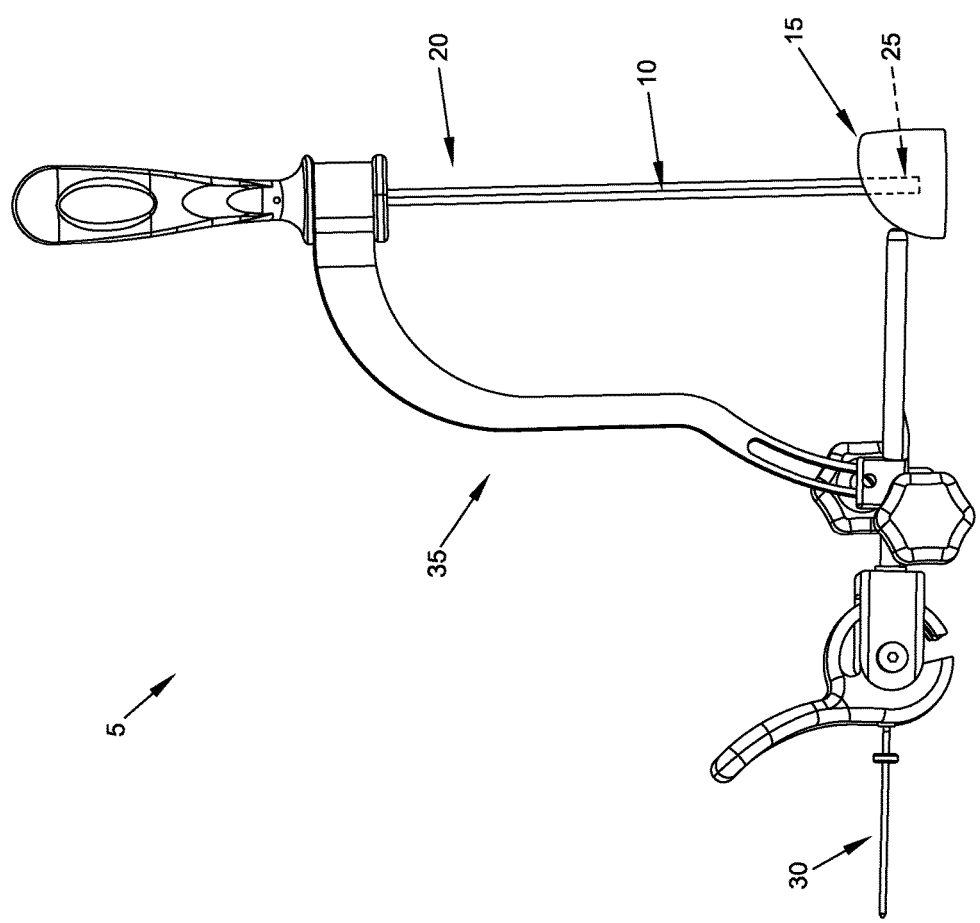

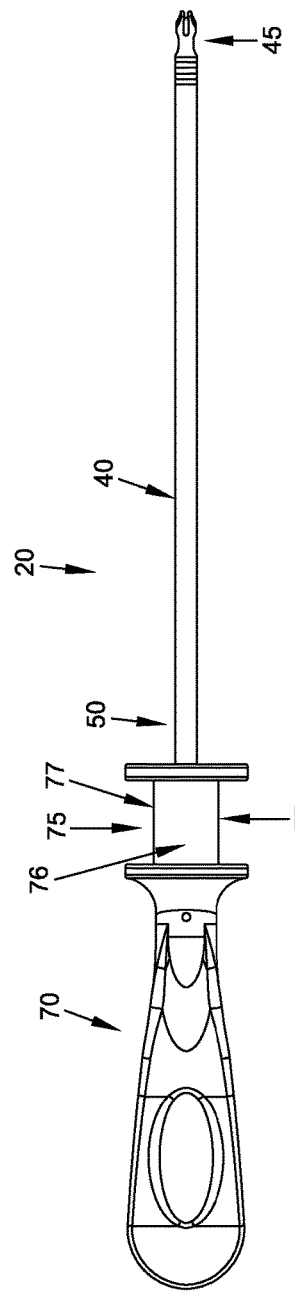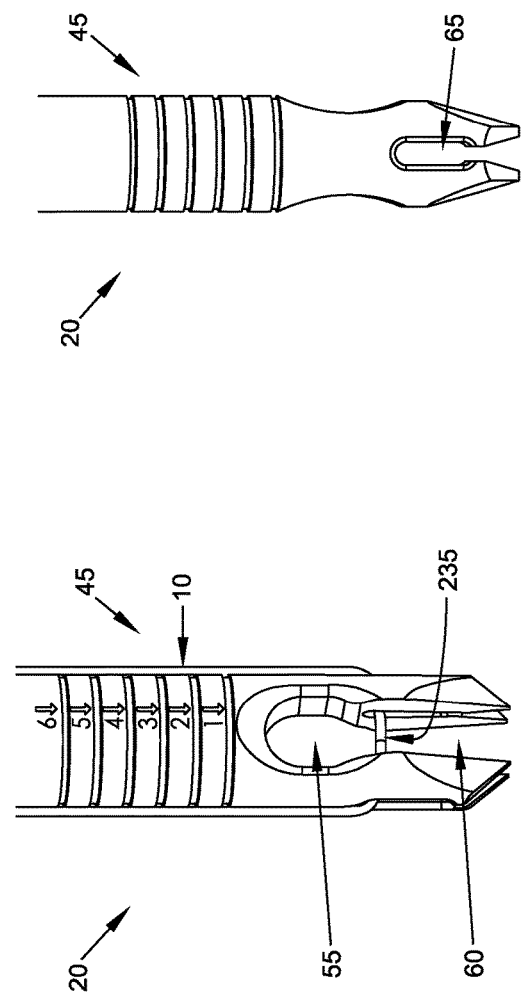

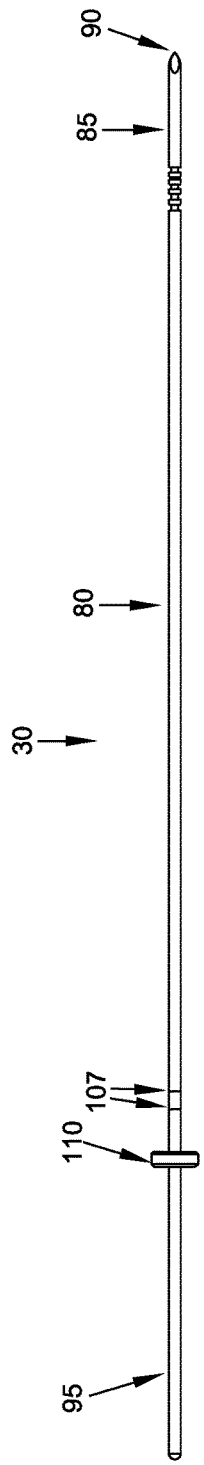
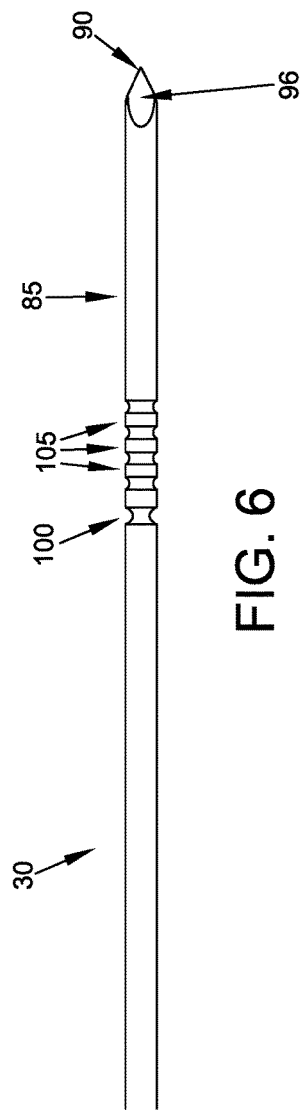
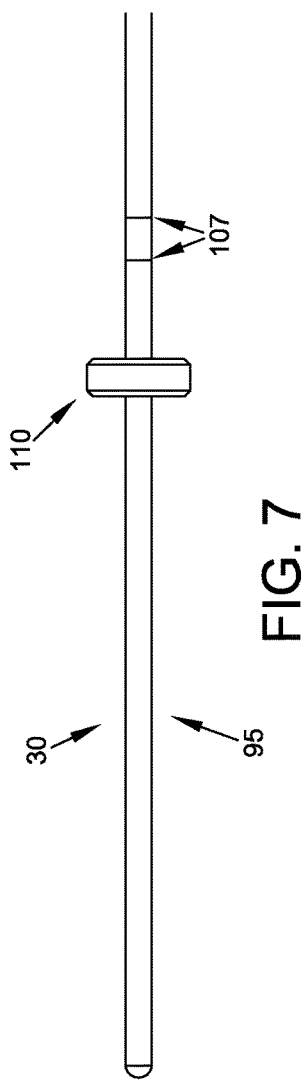

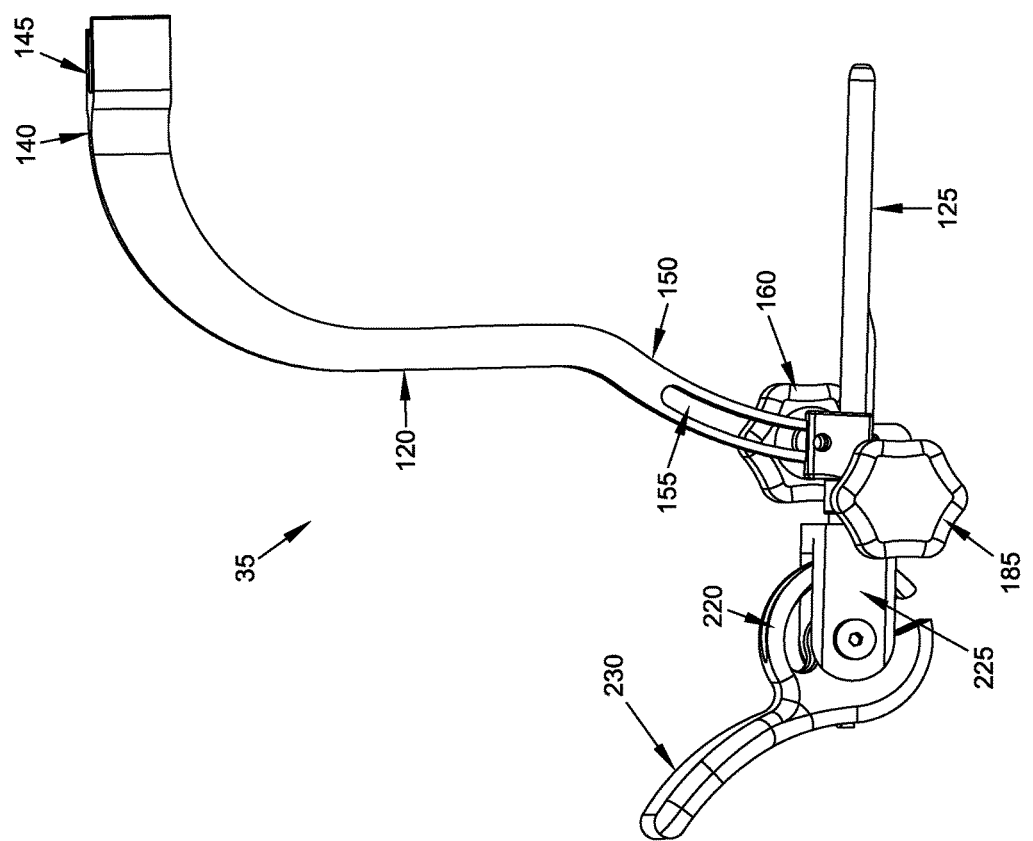

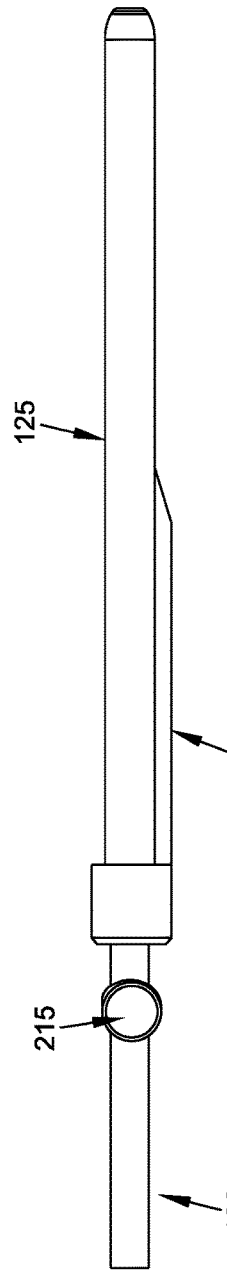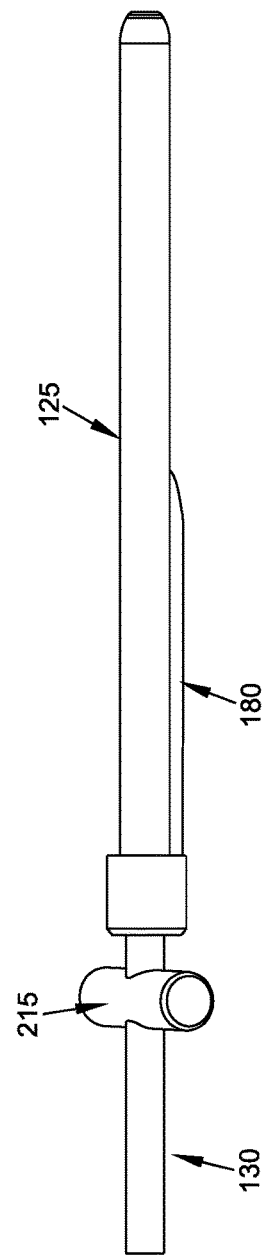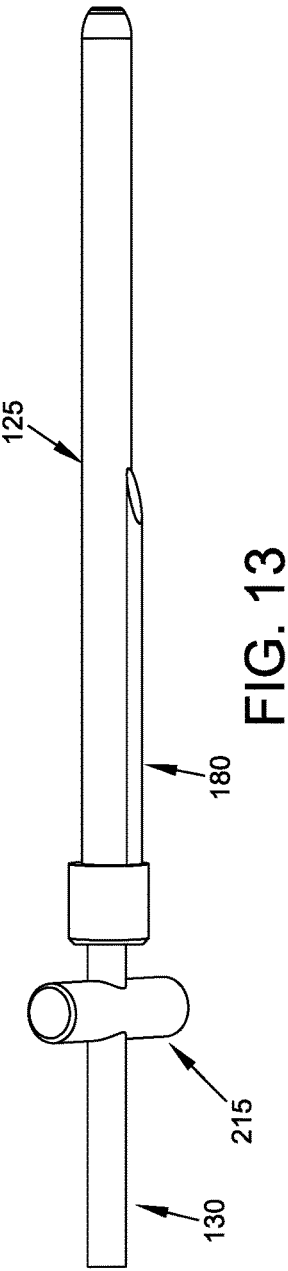

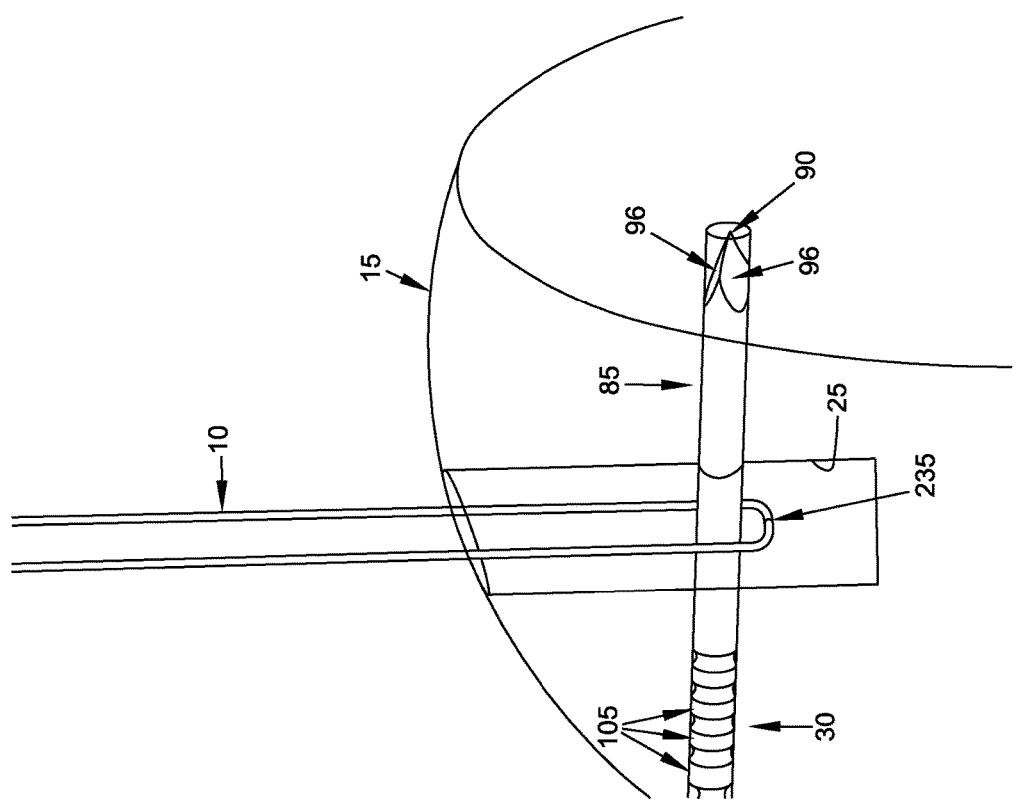

METHOD AND APPARATUS FOR ATTACHING AN ELONGATED OBJECT TO BONE

REFERENCE TO PENDING PRIOR PATENT APPLICATIONS

This patent application is a continuation of prior U.S. patent application Ser. No. 13/370,138, filed Feb. 9, 2012 by Nathan B. Snyder et al. for METHOD AND APPARATUS FOR ATTACHING AN ELONGATED OBJECT TO BONE, which patent application in turn claims benefit of prior U.S. Provisional Patent Application Ser. No. 61/441,121, filed Feb. 9, 2011 by Nathan B. Snyder et al. for SURGICAL WIRE SUTURE ANCHOR DEVICE AND SURGICAL TECHNIQUE OF EMPLOYING THE SAME.

The above-identified patent applications are hereby incorporated herein by reference.

FIELD OF THE INVENTION

This invention relates to surgical methods and apparatus in general, and more particularly to surgical methods and apparatus for attaching an elongated object to bone.

BACKGROUND OF THE INVENTION

In many situations, soft tissue must be attached, or re-attached, to bone. By way of example but not limitation, it is common to repair a torn rotator cuff in the shoulder by re-attaching a torn tendon to the humerus. By way of further example but not limitation, it is common to repair a torn labrum in the hip by re-attaching the torn labrum to the acetabulum.

In these and other situations, the soft tissue attachment (or re-attachment) may be effected using a suture anchor. More particularly, a suture anchor, having one or more sutures attached thereto, is mounted to a bone, with the suture(s) being used to attach (or re-attach) the soft tissue to that bone. The suture anchor is typically set into a hole formed in the bone so that the suture anchor is recessed within the bone, with the suture(s) emanating from the bone hole and available to "tie down" soft tissue (e.g., a ligament, labrum, etc.) to the bone.

The suture anchor is sized, shaped and/or otherwise constructed so as to resist withdrawal of the suture anchor from the bone hole, e.g., the suture anchor may comprise screws threads or ribs on its outer surface for gripping the adjacent bone, or the suture anchor may comprise expanding wings for projecting into the side wall of the bone hole, or the suture anchor may be formed in the shape of a wedge so as to lock into the bone, etc.

The suture(s) are generally attached to the suture anchor by passing the suture(s) through an eyelet formed in the proximal end of the suture anchor, although in some cases the suture(s) may be attached to the distal end of the suture anchor or the suture(s) may be attached to an intermediate portion of the suture anchor. In any case, the suture(s) typically extend along the longitudinal axis of the suture anchor as they exit the bone hole. In practice, due to constraints on arthroscopically accessing the repair site, the location of appropriate bone mass for receiving the suture anchor, the disposition of the soft tissue which is to be attached (or re-attached) to the bone, etc., the suture(s) are typically attached to the soft tissue at an angle of between about 0°-50° to the longitudinal axis of the bone hole (i.e., at an angle of between about 0°-50° from the axis along which the suture(s) extend prior to exiting the bone hole).

As noted above, suture anchors generally rely on a friction or interference fit with the surrounding bone in order to resist pull-out of the suture anchor from the bone. Since the loads imposed on the suture anchor may be substantial, and since bone quality may vary from patient to patient, it is generally desirable to increase resistance to pull-out. However, with suture anchors relying on a friction or interference fit with the surrounding bone to resist pull-out, this generally results in the manufacture and use of larger bone anchors. In practice, it is common for "stronger" bone anchors (i.e., bone anchors having greater pull-out strength) to be about 5.0-6.5 mm in diameter, which in turn requires the formation of a bone hole of at least this diameter. This large bone anchor/bone hole configuration displaces a considerable amount of bone at the repair site, particularly where several suture anchors (and hence several bone holes) must be used to effect a repair. At the very least, the use of large suture anchors (and hence the creation of large bone holes) introduces significant trauma for the patient; and in some cases, the need to accommodate such large suture anchors may necessitate the suture anchor being placed dangerously close to an articulating surface of a joint, or to an edge of a bone, etc.

Additionally, in order to maximize the pull-out strength of the suture anchor, many suture anchors employ a construction which "grips" the side wall of the bone hole substantially all the way up to the surface of the bone, e.g., in the case of a screw-type suture anchor, the suture anchor includes screw threads which engage the side wall of the bone hole substantially all the way up to surface of the bone (a so-called "fully-threaded" suture anchor). While such a construction can be highly advantageous since it enables the suture anchor to securely grip against the hard cortical bone which lies near the surface of the bone, it also results in the bone anchor effectively occupying the entire diameter of the bone hole all the way up to the surface of the bone. As a result, the body of the suture anchor acts as something of a dam to impede the flow of bone marrow elements from their origin at the interior of the bone to the site of the soft tissue attachment to the bone. Since these bone marrow elements contain important biological factors which facilitate tendon and bone healing, such "fully-threaded" suture anchors and related devices can significantly impede the healing process.

In addition to the foregoing, the complex mechanical nature of many of the suture anchors requires intricate manufacturing and assembly processes. This drives up suture anchor costs, which in turn drives up the cost of the surgical procedure.

Thus there is a need for a new and improved approach for attaching suture to bone which addresses the deficiencies of the prior art.

SUMMARY OF THE INVENTION

These and other objects are addressed by the provision and use of a novel system for attaching an elongated object (e.g., suture) to bone.

In one form of the present invention, there is provided apparatus for attaching an elongated object to bone, the apparatus comprising:

a surgical wire comprising a distal end and a proximal end, and a break joint disposed intermediate the distal end and the proximal end.

In another form of the present invention, there is provided a method for attaching an elongated object to bone, the method comprising:

forming a hole in the bone;

positioning a loop of the elongated object in the hole;

advancing a surgical wire into the bone so that the surgical wire is directed toward a location within the interior of the loop; and severing the surgical wire intermediate its length so as to create a distal portion and a remainder portion and, if the distal portion of the surgical wire does not extend through the loop, further advancing the distal portion of the surgical wire so that it extends through the loop.

In another form of the present invention, there is provided a method for attaching a suture to bone, the method comprising:

forming a hole in a bone;

mounting a suture to a suture holder of the sort comprising a shaft having a distal end and a proximal end, a crossbore formed on the distal end of the shaft, and a slot extending from the crossbore to the distal tip of the suture holder, the suture being mounted to the suture holder so that a loop of suture is disposed distal to the crossbore and traverses the slot;

mounting the suture holder to an aiming guide, and mounting the aiming guide to a base having a bore formed therein, such that the bore of the base is aligned with the crossbore of the suture holder;

inserting the distal end of the suture holder into the hole formed in the bone so that the loop of suture is disposed within the bone hole;

inserting a tissue protector through the bore of the base, wherein the tissue protector comprises a lumen, the lumen being aligned with the crossbore of the suture holder, and wherein the lumen of the tissue protector receives a collet having a lumen and a compressible portion for selectively reducing the size of the lumen, the lumen of the collet being aligned with the crossbore of the suture holder;

inserting a surgical wire through the lumen of the collet, into the bone and across the crossbore of the suture holder so that the distal end of the surgical wire extends through the loop of suture, the surgical wire comprising a break joint located proximal to the distal end of the surgical wire;

causing the compressible portion of the collet to grip the surgical wire distal to the break joint;

applying torque to the proximal end of the wire so as to sever the surgical wire at the break joint;

causing the compressible portion of the collet to release the surgical wire;

advancing the proximal end of the surgical wire distally so as to move the severed distal end of the surgical wire distally, so that the severed distal end of the surgical wire sits even with or distal to the outer surface of the bone;

removing the proximal end of the surgical wire, the tissue protector, the collet and the suture holder, leaving the loop of suture attached to the bone by means of the severed distal end of the wire extending across the bone hole and through the loop of suture.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 1 is a schematic view of a novel system for attaching an elongated object (e.g., suture) to bone, wherein the novel system comprises a suture holder, a surgical wire and a deployment assembly;

FIGS. 2-4 are schematic views showing a preferred form of the suture holder of the novel system of FIG. 1;

FIGS. 5-7 are schematic views showing a preferred form of the surgical wire of the novel system of FIG. 1;

FIGS. 8-15 are schematic views showing a preferred form of the deployment assembly of the novel system of FIG. 1; and FIGS. 16-30 are schematic views showing a preferred method for attaching a suture to bone using the novel system of FIG. 1.

DETAILED DESCRIPTION OF THE PREFERRED EMBODIMENTS

Figure 9:
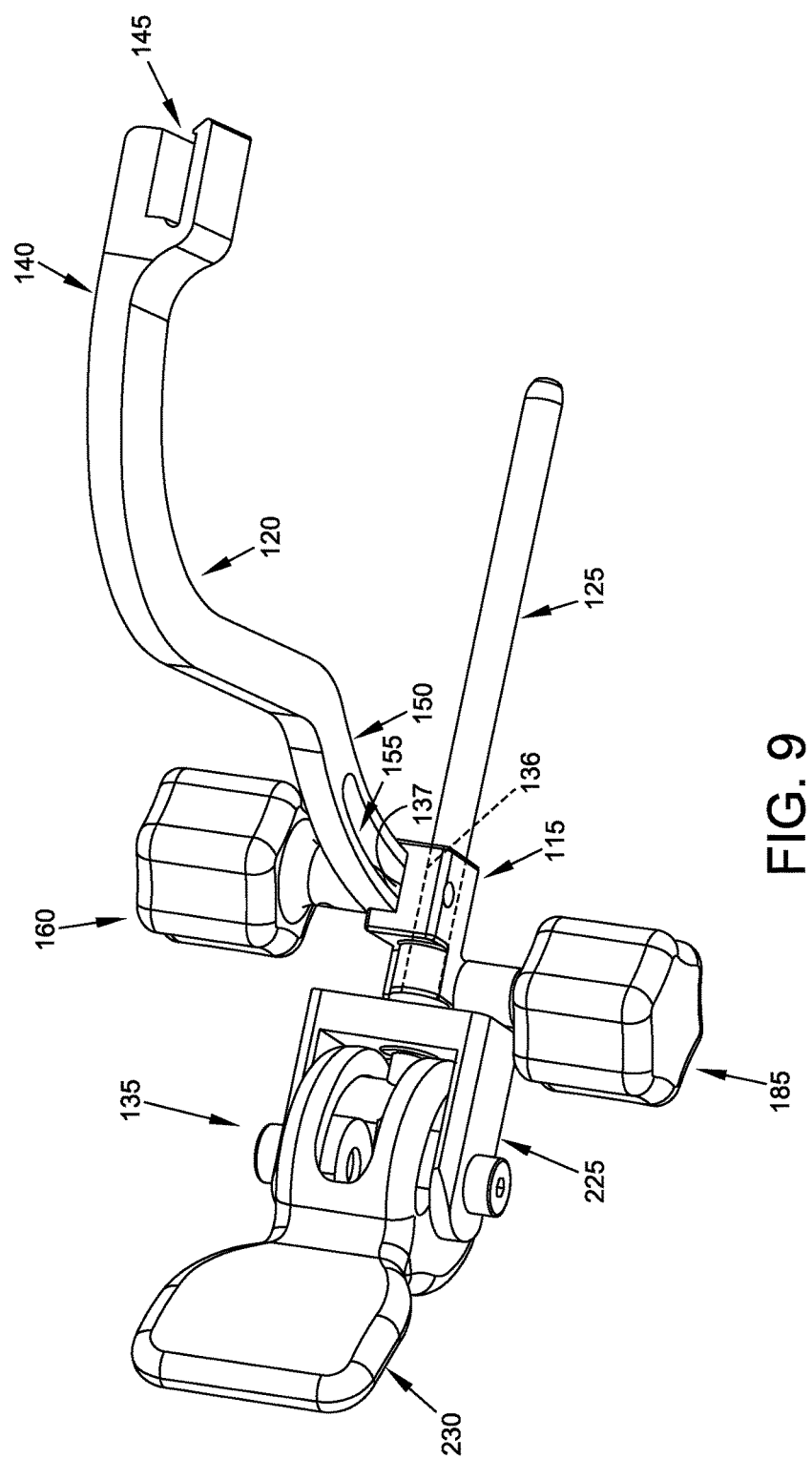
Figure 10:
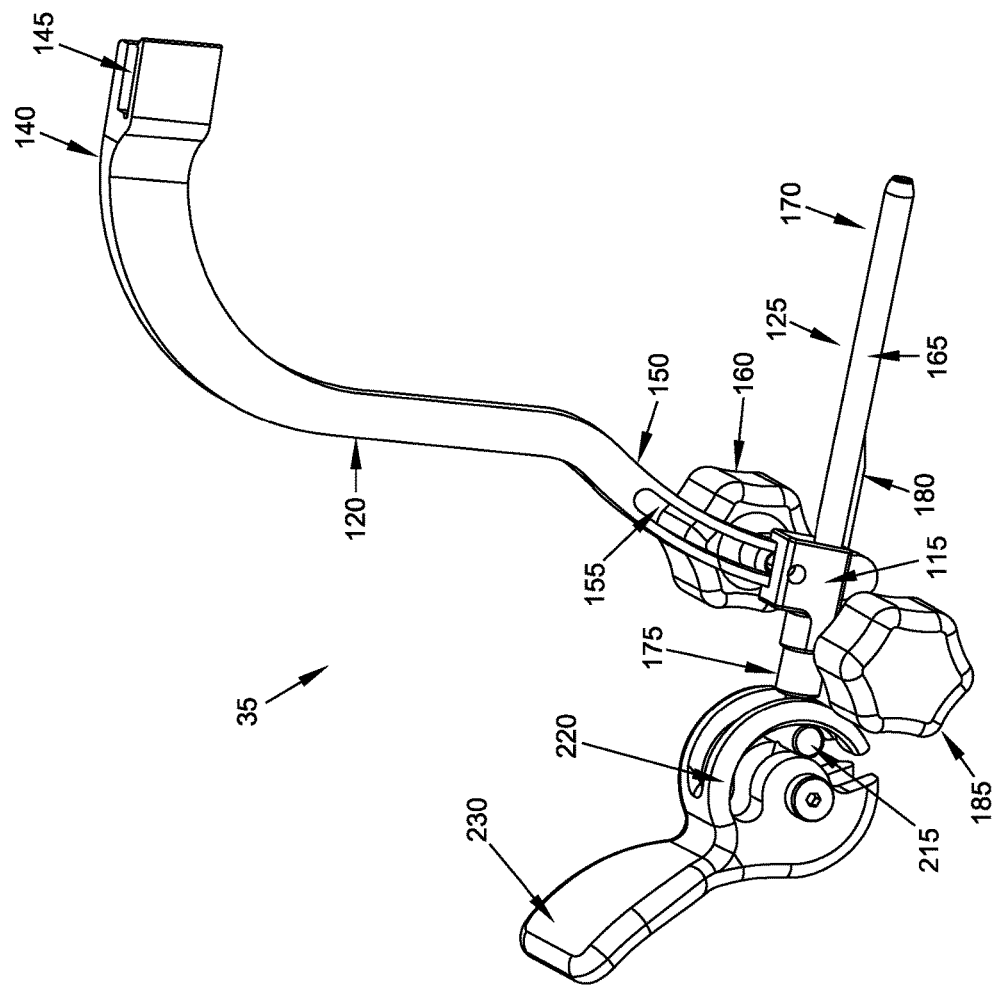
Figure 14:
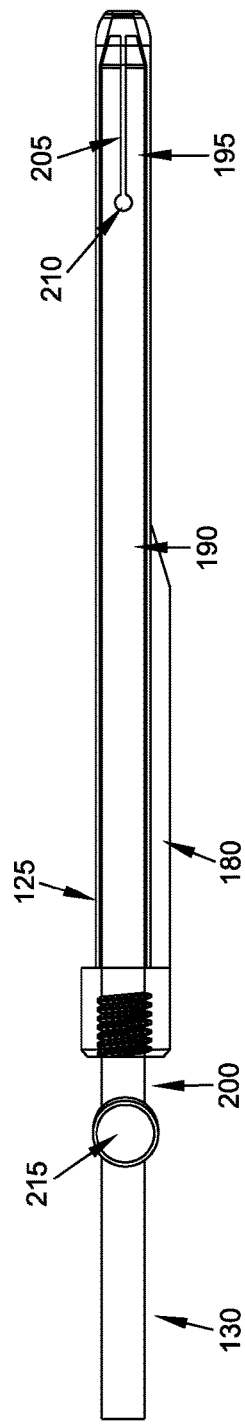
Figure 15:
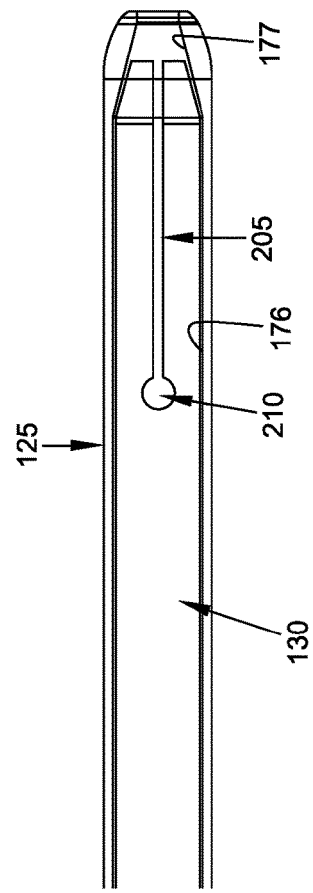

The present invention comprises the provision and use of a novel system for attaching an elongated object (e.g., suture) to bone. For clarity of description, the novel system will hereinafter be described in the context of attaching a suture to bone; however, it should be appreciated that the novel system may also be used to attach more than one suture to bone, or to attach a different type of elongated object (e.g., a ligament, tendon, muscle, etc.) to bone, etc.

In one preferred form of the present invention, and looking now at FIG. 1, there is provided a novel system 5 for attaching a suture 10 to a bone 15. Novel system 5 generally comprises a suture holder 20 for supporting suture 10 in a bone hole 25 formed in bone 15, a surgical wire 30 having a distal end (not shown in FIG. 1) for disposition across bone hole 25 and attaching suture 10 to bone 15, and a deployment assembly 35 for advancing the distal end of surgical wire 30 across bone hole 25 and then separating the distal end of the surgical wire from the remainder of the surgical wire, whereby to leave the separated distal end of the surgical wire embedded in bone 15, spanning bone hole 25 and attaching the suture 10 to bone 15, when the remainder of the surgical wire is withdrawn from the surgical site, as will hereinafter be discussed in further detail.

Suture holder 20 is shown in detail in FIGS. 2-4. Suture holder 20 generally comprises a shaft 40 having a distal end 45 and a proximal end 50. Distal end 45 comprises a crossbore 55 sized to receive the distal end of surgical wire 30 as will hereinafter be discussed, a first slot 60 extending between crossbore 55 and the distal tip of shaft 40, and a second slot 65 sized to receive suture 10. First slot 60 has a diameter which is larger than the diameter of surgical wire 30, such that the severed distal end of surgical wire 30 can pass out of crossbore 55 and through first slot 60 when suture holder 20 is being withdrawn from bone hole 25, as will hereinafter be discussed. Second slot 65 extends perpendicular to crossbore 55 and first slot 60. The proximal end 50 of shaft 40 is secured to a handle 70. Handle 70 is cut away adjacent to its distal end so as to form a substantially rectangular cross-section 75 comprising a pair of elongated faces 76 (only one of which is shown in FIG. 2) connected by a pair of shortened faces 77. Elongated faces 76 extend substantially parallel to crossbore 55 and first slot 60. As a result of this construction, by controlling the disposition of elongated faces 76 about the longitudinal axis of shaft 40 and handle 70, the disposition of crossbore 55 and first slot 60 can also be controlled about the longitudinal axis of shaft 40 and handle 70, as will hereinafter be discussed in further detail.

Surgical wire 30 is shown in detail in FIGS. 5-7. Surgical wire 30 generally comprises a shaft 80 having a distal end 85 (terminating in a sharp point 90) and a proximal end 95. In one preferred form of the invention, sharp point 90 is formed at the convergence of a plurality of planar faces 96 disposed at the distal end of surgical wire 30, e.g., sharp point 90 is formed at the apex of three planar faces 96 disposed at the distal end of surgical wire 30, or sharp point 90 is formed at the apex of four planar faces 96 disposed at the distal end of surgical wire 30, etc. Alternatively, sharp point 90 may be formed by a conical construct at the distal end of surgical wire 30. However, forming sharp point 90 by the convergence of a plurality of planar surfaces 96 is generally preferred, since such a construction facilitates drilling the surgical wire 30 into bone. A "fuse" or "break joint" 100 connects distal end 85 to the remainder of shaft 80. Fuse or break joint 100 is engineered so as to normally maintain the structural integrity (e.g., linearity, column strength, torqueability, etc.) of surgical wire 30, but is also engineered so that it will cleanly break upon delivery of a pre-determined level of torque to the fuse or break joint 100, as will hereinafter be discussed in further detail. In one preferred form of the invention, fuse or break joint 100 is formed by appropriately thinning the diameter of shaft 80 at the fuse or break joint, e.g, by means of a peripheral surface groove. A plurality of ribs 105 may be formed on distal end 85, distal to fuse or break joint 100. At least one length marker 107, and a stop 110, are formed on the proximal end of shaft 80. The at least one length marker 107 is disposed distal to stop 110.

Deployment assembly 35 is shown in detail in FIGS. 8-15. Deployment assembly 35 generally comprises a base 115, an aiming guide 120, a tissue protector 125, a collet 130 and a collet actuator 135.

Base 115 comprises a bore 136 for slidably receiving tissue protector 125 therein, and a slot (not shown) communicating with and extending parallel to bore 136 for receiving a guide fin (see below) attached to tissue protector 125, and a slot 137 for slidably receiving aiming guide 120 therein.

Aiming guide 120 generally comprises a first end 140 which includes a rectangular slot 145 for receiving the rectangular cross-section 75 of handle 70 of suture holder 20, and a second end 150 which includes a slot 155 for adjustably mounting aiming guide 120 in slot 137 of base 115 via a thumbscrew 160.

Tissue protector 125 comprises a hollow shaft 165 having a distal end 170, a proximal end 175, and a central lumen 176 extending therebetween. Tissue protector 125 is sized to slidably receive collet 130 therein, as will hereinafter be discussed. The central lumen 176 of tissue protector 125 narrows at the distal end of the tissue protector at an inclined annular shoulder 177. Tissue protector 125 is adapted to be slidably mounted in bore 136 of base 115 and includes a guide fin 180 along a portion of its length in order to keep tissue protector 125 from rotating relative to base 115 (guide fin 136 is slidably received in the aforementioned slot (not shown) formed in base 115 and communicating with and extending parallel to bore 136). A thumbscrew 185 allows tissue protector 125 to be locked in position relative to base 115.

Figure 26:
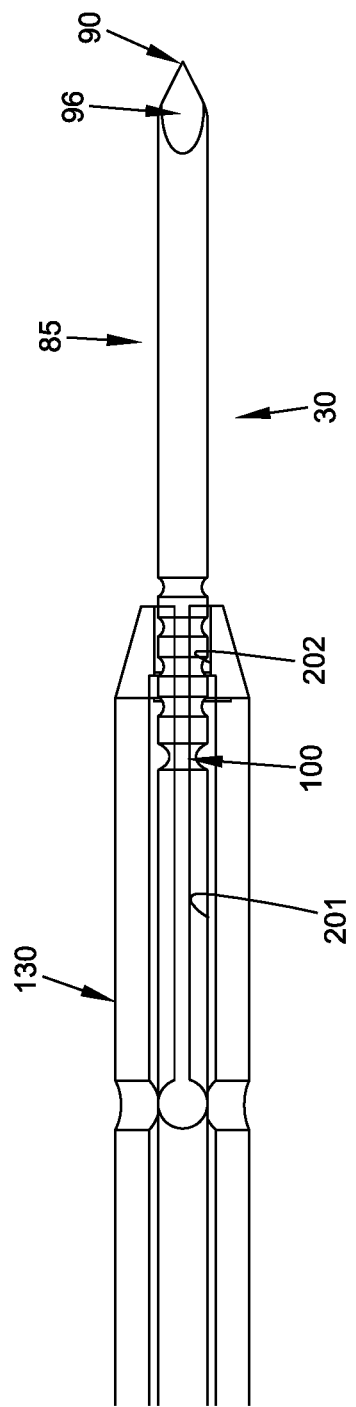

Collet 130 comprises a hollow shaft 190 having a distal end 195, a proximal end 200 and a central lumen 201 (FIG. 26) extending therebetween. Central lumen 201 preferably narrows at the distal end of hollow shaft 190, e.g., as shown at 202 (FIG. 26). Hollow shaft 190 of collet 130 (i.e., central lumen 201 of hollow shaft 190) is sized to receive surgical wire 30 therein, as will hereinafter be discussed. The distal end 195 of collet 130 includes a slot 205 terminating in a stress relief hole 210, whereby to enable the distal end 195 of collet 130 to be compressed inwardly when collet 130 is forced distally into engagement with inclined annular shoulder 177 of tissue protector 125, as will hereinafter be discussed. A cam follower 215 is provided near the proximal end of collet 130 in order to allow collet actuator 135 to move collet 130 into, and out of, engagement with inclined annular shoulder 177 of tissue protector 125, as will hereinafter be discussed.

Collet actuator 135 comprises a cam 220 which is pivotally mounted to a frame 225, which is in turn mounted to tissue protector 125. Cam 220 receives cam follower 215 of collet 130, and has a selected geometry (i.e., non-circular) such that rotational movement of cam 220 relative to frame 225 will cause longitudinal movement of collet 130 relative to tissue protector 125 (and, in particular, longitudinal movement of collet 130 relative to inclined annular shoulder 177 of tissue protector 125, as will hereinafter be discussed in further detail). A lever 230 is provided for moving cam 220 relative to frame 225, and hence moving collet 130 relative to tissue protector 125. Preferably lever 230 is formed integral with cam 220.

In one preferred form of the invention, tissue protector 125, collet 130, frame 225 and cam 220/lever 230 are all pre-assembled into a single subassembly which may be mounted to base 115 as a unit when desired (see below). It will be appreciated that when tissue protector 125, collet 130, frame 225 and cam 220/lever 230 are so pre-assembled, cam follower 215 of collet 130 is mounted on the working surfaces of cam 220.

System 5 is preferably used in the following manner to attach suture 10 to bone 15.

Figure 17:
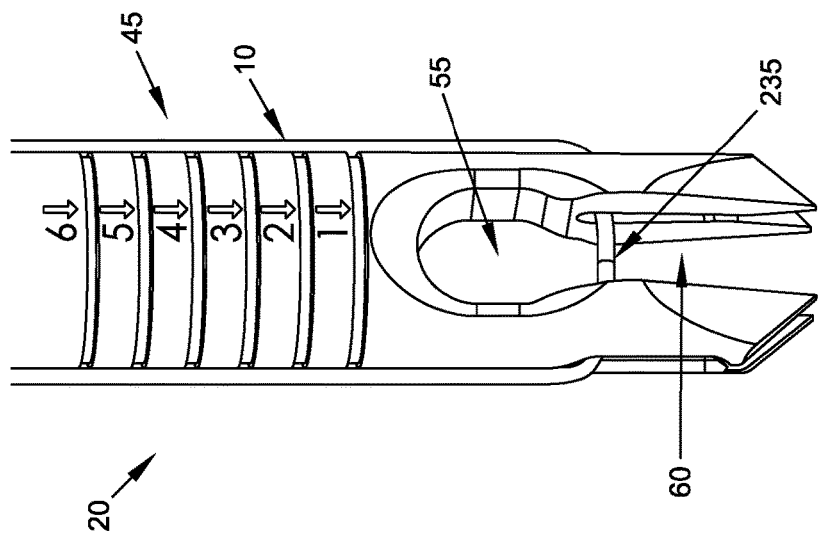
Figure 16:
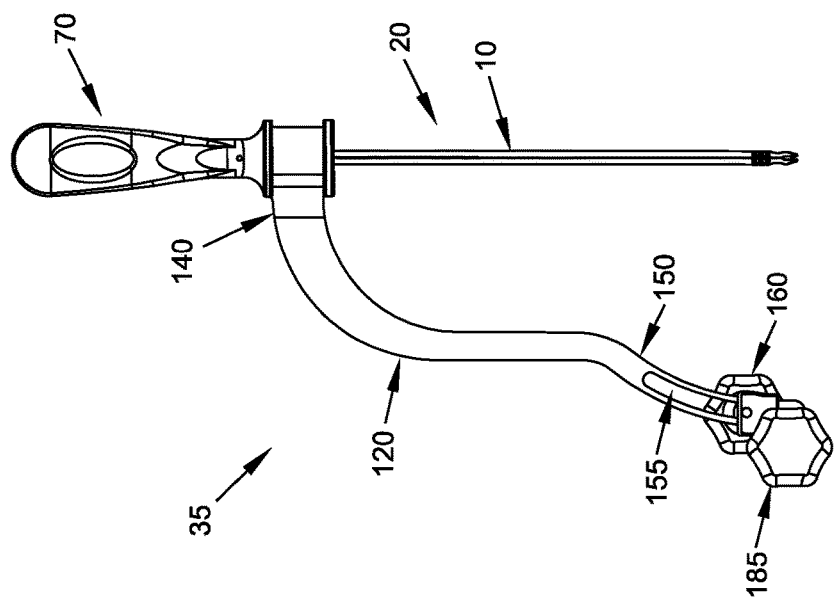

First, and looking now at FIGS. 16 and 17, suture 10 is loaded onto suture holder 20. This is done by extending suture 10 down the length of shaft 40 of suture holder 20, through second slot 65 of the suture holder so that the suture extends across the diameter of the shaft, and then back up along the length of shaft 40. This action causes suture 10 to form a loop 235 about the distal end of shaft 40, with the loop 235 residing on the far side (i.e., the distal side) of crossbore 55, and traversing first slot 60 in suture holder 20, in the manner shown in FIG. 17. The two free ends of suture 10 may then be manually held by the user against handle 70, or the two free ends of suture 10 may be releasably secured to suture mounts (not shown) formed on handle 70, etc.

At this point, suture holder 20 is preferably mounted to aiming guide 120 by positioning rectangular cross-section 75 of handle 70 in rectangular slot 145 of aiming guide 120, and aiming guide 120 is preferably mounted to base 115, in the manner shown in FIG. 16. Alternatively, suture holder 20 may be mounted to aiming guide 120 prior to loading suture 10 onto suture holder 20. In either case, it will be appreciated that upon positioning rectangular cross-section 75 of handle 70 in rectangular slot 145 of aiming guide 120, and mounting aiming guide 120 to base 115, crossbore 55 and first slot 60 of suture holder 20 will be aligned with base 115 of deployment assembly 35, with crossbore 55 being co-axial with bore 136 of base 115.

Figure 18:
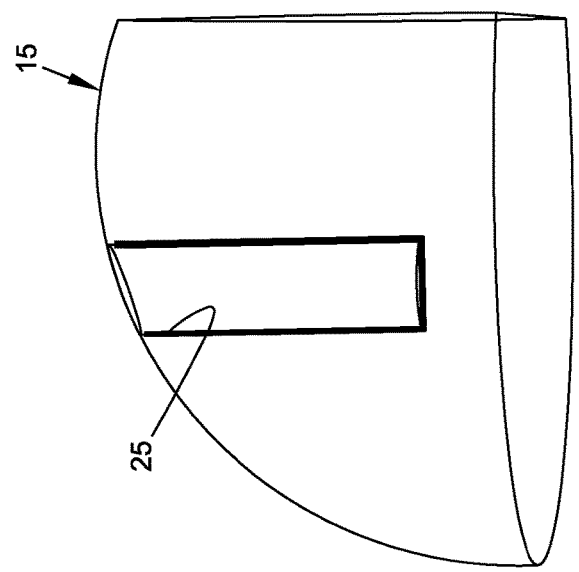

Next, and looking now at FIG. 18, a hole 25 is formed in bone 15. Alternatively, if desired, hole 25 may be formed in bone 15 before suture 10 is loaded onto suture holder 20 and suture holder 20 is mounted to aiming guide 120 and aiming guide 120 is mounted to base 115, etc. Significantly, the size of the hole 25 formed in bone 15 may be significantly smaller than the bone holes used for conventional, high pull-out strength anchors, since bone hole 25 only needs to accommodate the suture 10 (and, during deployment, the relatively narrow suture holder 20) and does not need to accommodate the relatively large body of a suture anchor. By way of example but not limitation, where a No. 2 size suture is to be attached to bone 15, bone hole 25 may have a diameter of only about 3.8 mm, which is significantly smaller than the bone holes normally required for typical high pull-out strength anchors (which anchors are themselves about 5.0-6.5 mm diameter, and which therefore require bone holes of at least this diameter). In this respect it will be appreciated that inasmuch as the cross-section of the bone hole is a function of $(pi)r^2$, a 3.8 mm diameter bone hole has a cross-section which is only about 58% of a 5.0 mm diameter bone hole, and which is only about 34% of a 6.5 mm diameter bone hole. Thus, the present invention imposes significantly less trauma on the host bone than a high pull-out strength anchor.

Figure 19:
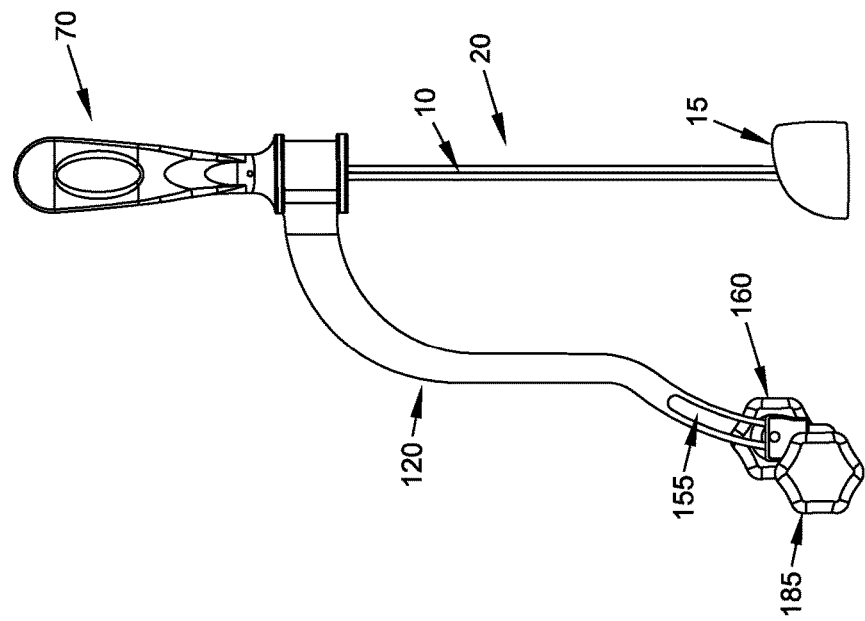
Figure 20:
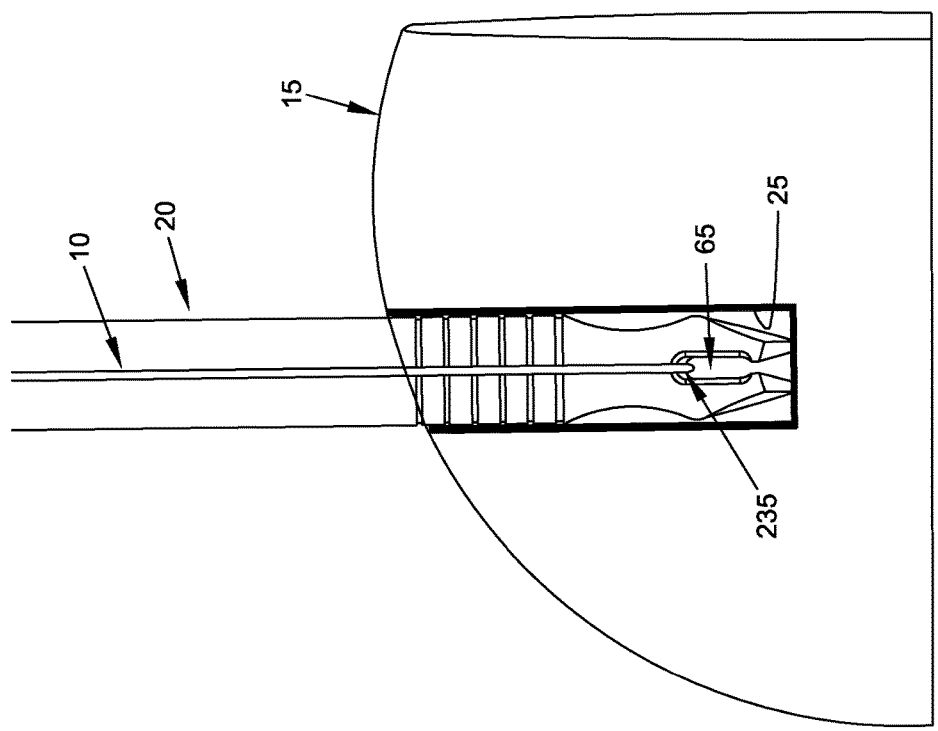

At this point, and looking now at FIGS. 19 and 20, the apparatus is manipulated so that the distal end of suture holder 20 is inserted into hole 25 in bone 15, with the loop 235 of suture residing inside the bone hole.

Next, an incision is made through the skin so as to expose bone 15 from the direction of base 115.

Figure 21:
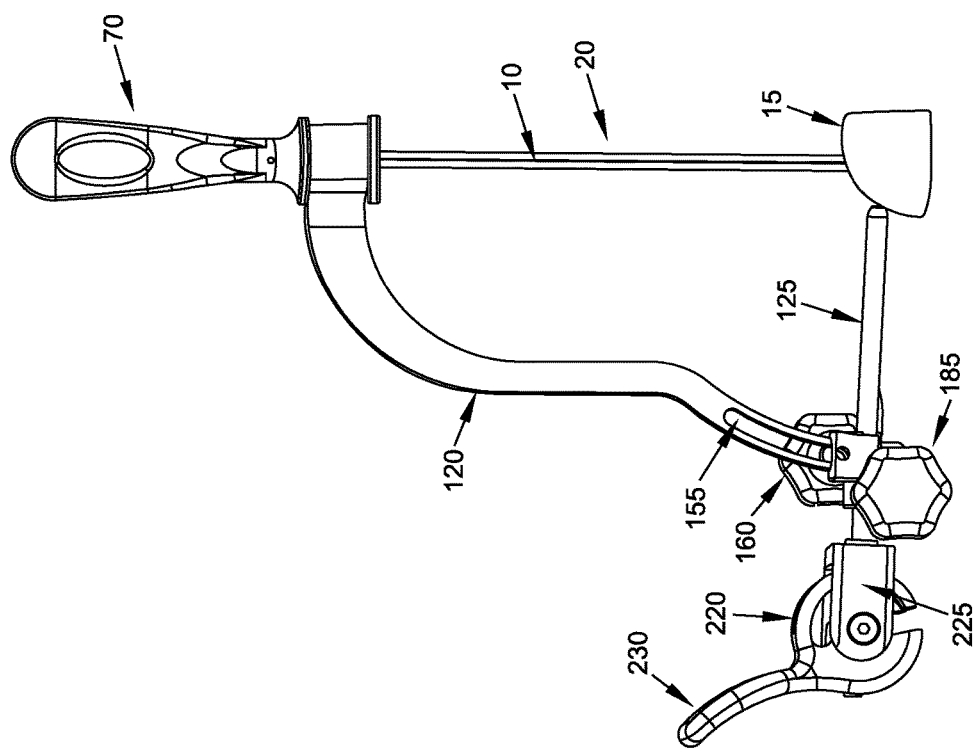

Then, and looking now at FIG. 21, tissue protector 125, having a collet 130 received therein, and having frame 225 and cam 220/lever 230 mounted thereon, is mounted to base 115. At this point lever 230 is in its "retracted" position (FIG. 21) so that collet 130 is withdrawn from inclined annular shoulder 177 of tissue protector 125, i.e., so that the distal end of the collet is in its relaxed, expanded condition. It will be appreciated that, due to the orientation of the crossbore 55 and first slot 60 relative to rectangular cross-section 75 of handle 70, and due to the orientation of rectangular slot 145 of aiming guide 120 relative to base 115, tissue protector 125 and collet 130 will be aligned with crossbore 55 of suture holder 20 at this point and, significantly, the central lumen 175 of tissue protector 125 and the central lumen 201 of collet 130 will be oriented toward the interior of the loop 235 of the suture 10 carried by suture holder 20.

At this point, the angular disposition of aiming guide 120 relative to base 115 is adjusted as desired and then locked in position using thumbscrew 160, and the longitudinal disposition of tissue protector 125 relative to bone 15 is adjusted as desired and then locked in position using thumbscrew 185.

Figure 22:
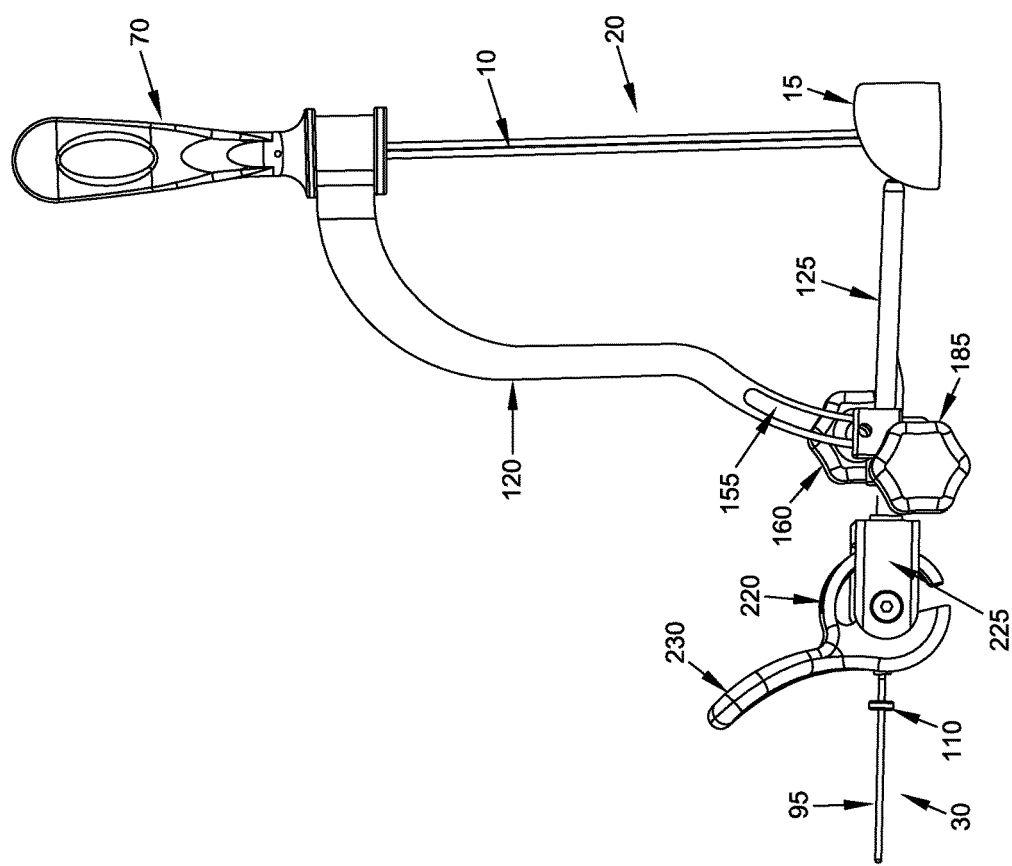
Figure 23:
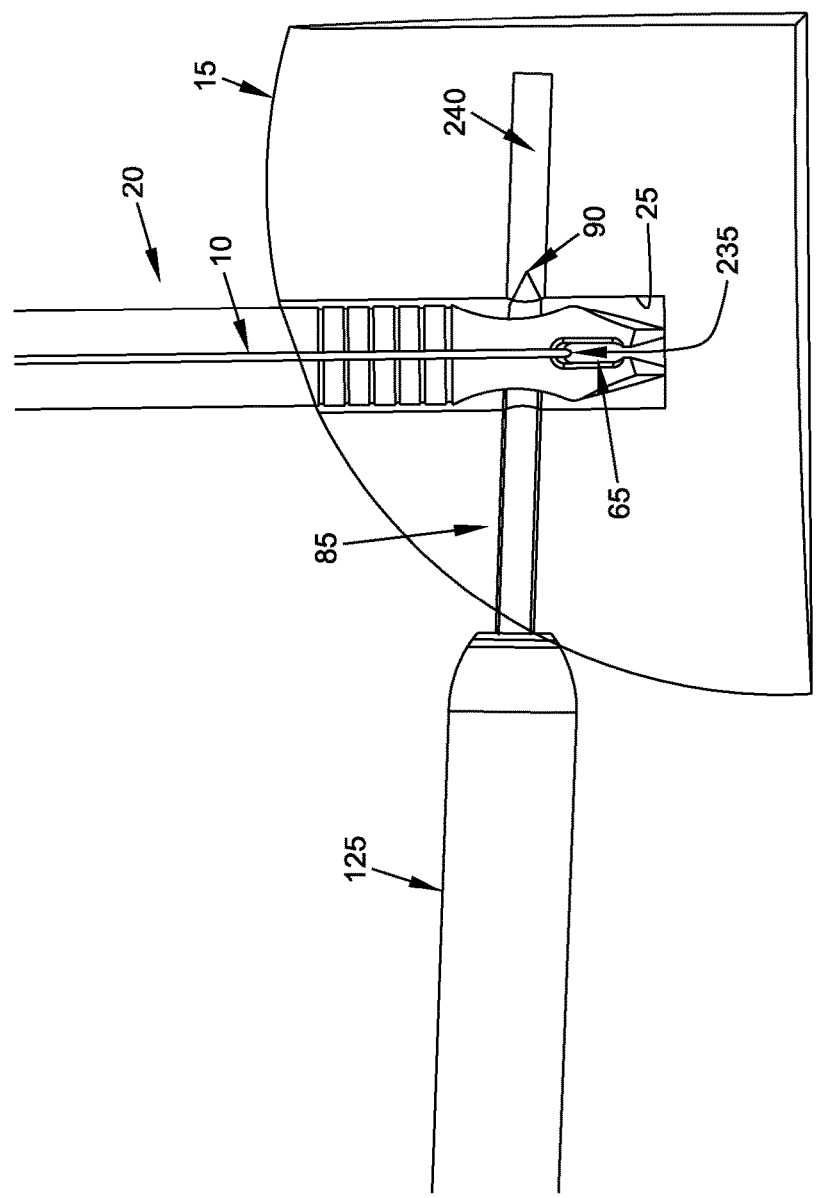

Next, and looking now at FIGS. 22 and 23, surgical wire 30 is advanced through collet 130 and tissue protector 125, and then advanced through bone 15, so that the sharp point 90 at the distal end of surgical wire 30 extends through crossbore 55 in suture holder 20 and starts to enter the bone on the far side of the bone tunnel. As this occurs, surgical wire 30 extends across the interior of the loop 235 of suture 10 carried by suture holder 20. Length markers 107 on surgical wire 30 may be used to help ensure that the distal end of surgical wire 30 spans hole 25 in bone 15 before forward movement of surgical wire 30 is stopped. At the same time, however, length markers 107 on surgical wire 30 help ensure that forward movement of surgical wire 30 stops before fuse or break joint 100 of surgical wire 30 passes out of the distal end of collet 130. Preferably, surgical wire 30 is advanced by drilling the surgical wire into the bone—in this case, the level of torque applied to the proximal end of the surgical wire is kept below the level of torque required to break the surgical wire at fuse or break joint 100. Stated another way, fuse or break joint 100 is engineered so as to withstand the level of torque required to drill surgical wire 30 into bone 15. If desired, a seat for surgical wire 30 may be pre-drilled in bone 15 (see, for example, the bore 240 shown in FIG. 23). Alternatively, surgical wire 30 may be advanced into the bone by tapping on the proximal end of the wire—this method of advancement does not impose a torque load on fuse or break joint 100 of the surgical wire.

At this point, it can be desirable to confirm that surgical wire 30 is properly disposed in crossbore 55 of suture holder 20 (and hence surgical wire 30 extends across the interior of loop 235 of suture 10 carried by suture holder 20). Such confirmation may be done by taking an X-ray image, using fluoroscopy, separating suture holder 20 from aiming guide 120 and removing the suture holder from the bone hole so as to check if the suture loop 235 is captured by surgical wire 30, etc. If it is determined that surgical wire 30 is not properly disposed in crossbore 55, surgical wire 30 can be backed out of the bone and the foregoing process repeated so that surgical wire 30 is properly disposed in crossbore 55 of suture holder 20. Thus it will be appreciated that with the present invention, successful capture of suture loop 235 can be ensured prior to committing to the deployment of the implant in the bone.

Figure 24:
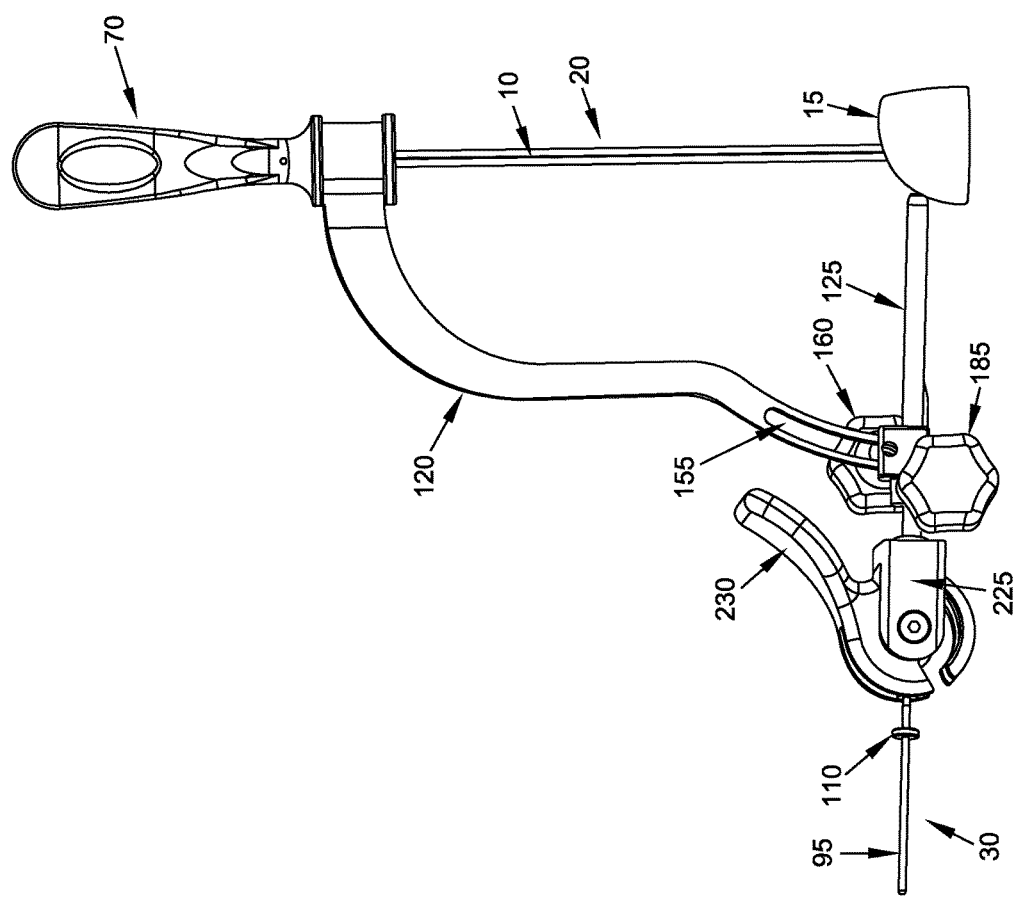
Figure 25:
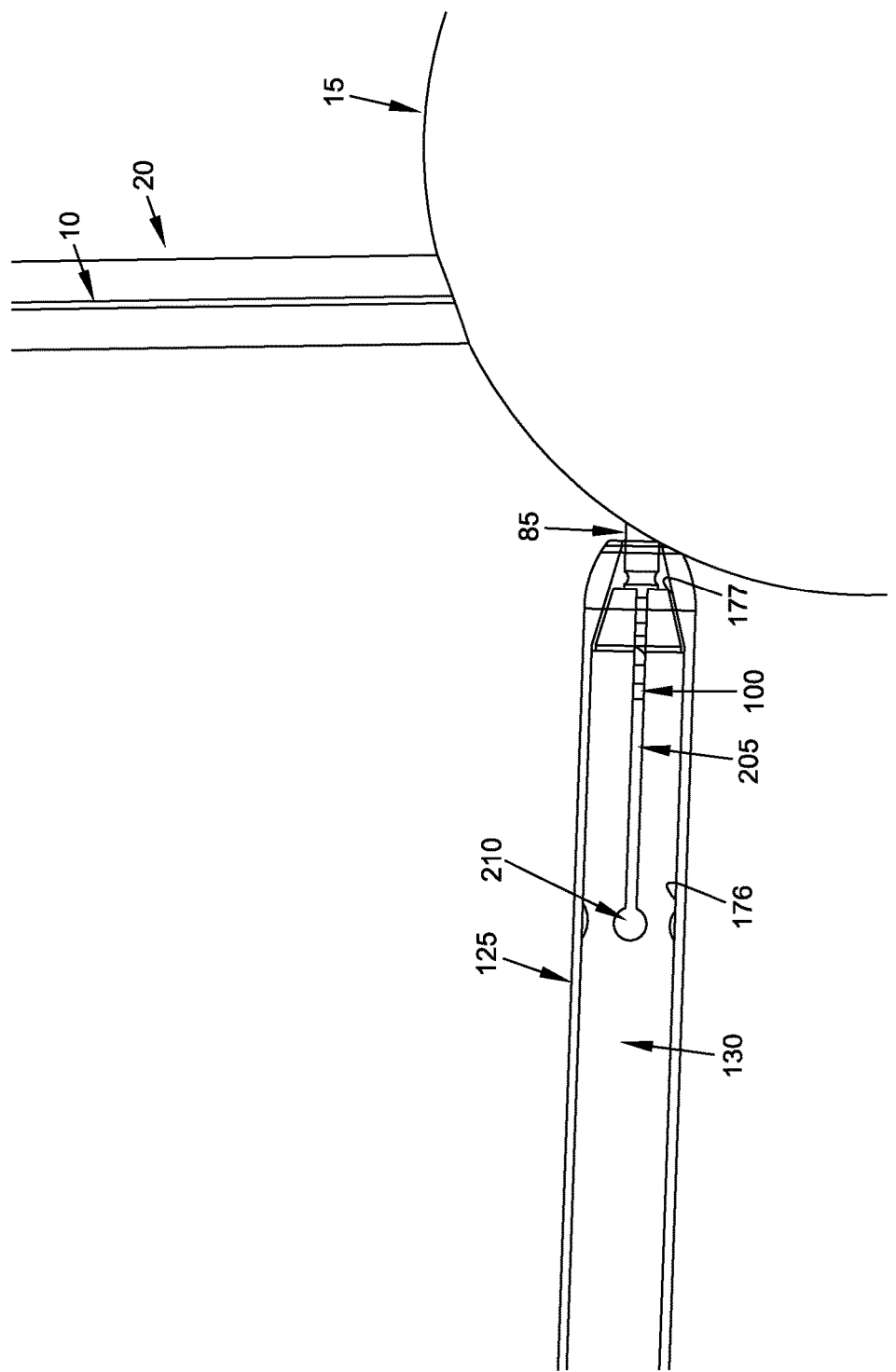

With surgical wire 30 properly disposed in crossbore 55 of the suture holder 20, and looking now at FIGS. 24-26, lever 230 of deployment assembly 35 is moved to its "forward" position (FIG. 24), causing the distal end of collet 130 to be driven against inclined annular shoulder 177 of tissue protector 125, whereupon the distal end of collet 130 is compressed down on surgical wire 30, distal to fuse or break joint 100, whereby to securely grip the distal end of the surgical wire distal to fuse or break joint 100.

Then, with the distal end of surgical wire 30 held against rotation by collet 30 (which is itself held against rotation by virtue of the engagement of its cam follower 215 with cam 220, and the engagement of cam 220 with frame 225, and the engagement of frame 225 with the tissue protector 125, and the engagement of tissue protector 125 with base 115), the proximal end of surgical wire 30 is turned with sufficient force to break the surgical wire at fuse or break joint 100, with the distal end of the surgical wire (i.e., that portion of the surgical wire distal to fuse or break joint 100) extending into bone 15 and across hole 25 in bone 15, and hence extending through loop 235 of suture 10.

Figure 27:
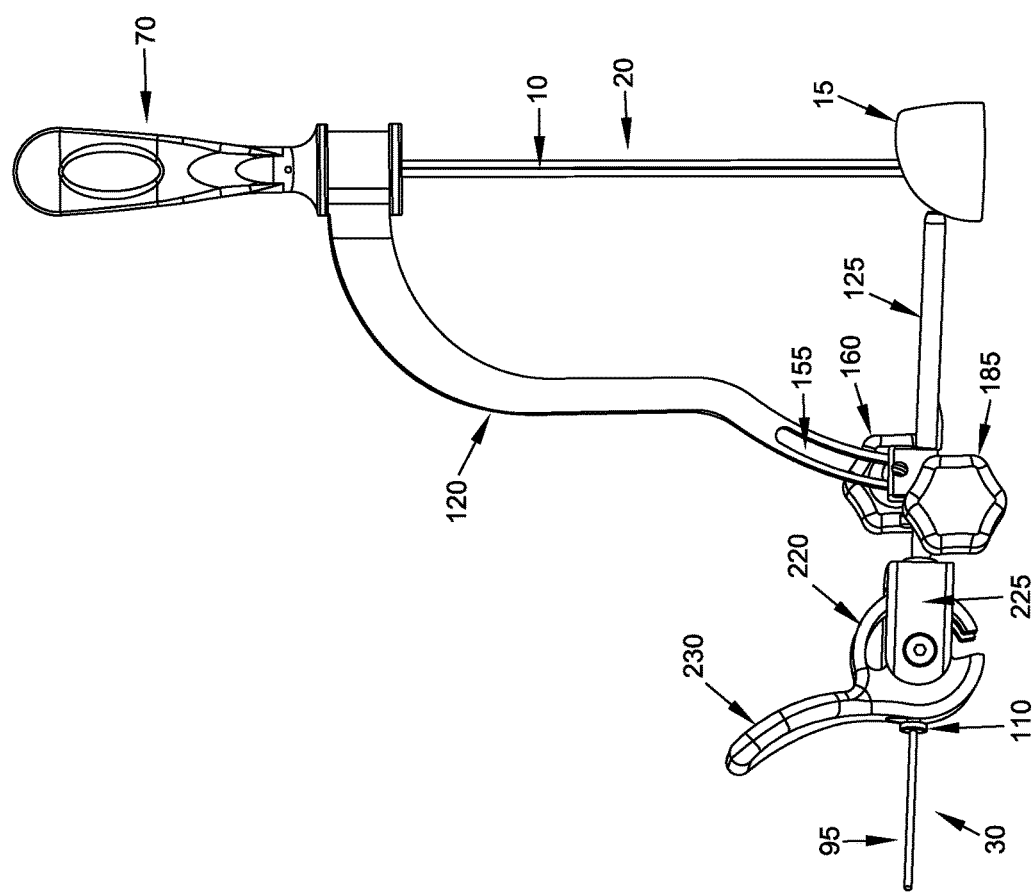

Next, and looking now at FIG. 27, lever 230 is moved back to its "retracted" position, thereby allowing collet 130 to move proximally and release its grip on surgical wire 30. Then, the proximal end of surgical wire 30 is advanced once again toward bone 15 (e.g., by tapping), thereby driving the severed distal end of surgical wire 30 further into the bone and hence further across bone hole 25. Stop 110 on the proximal end of surgical wire 30 ensures that the severed distal end of surgical wire 30 is driven an appropriate distance into bone 15 (e.g., far enough so that the severed distal end of surgical wire 30 is completely disposed within the bone, but not so far that the proximal-most portion of the severed distal end of surgical wire 30 enters bone hole 25). At this point the severed distal end of surgical wire 30 is securely fixed in the bone on either side of bone hole 25, with the severed distal end of surgical wire 30 extending through loop 235 of suture 10. Ribs 105 formed on the severed distal end of surgical wire 30 help enhance fixation of the severed distal end of surgical wire 30 in the bone.

Figure 28:
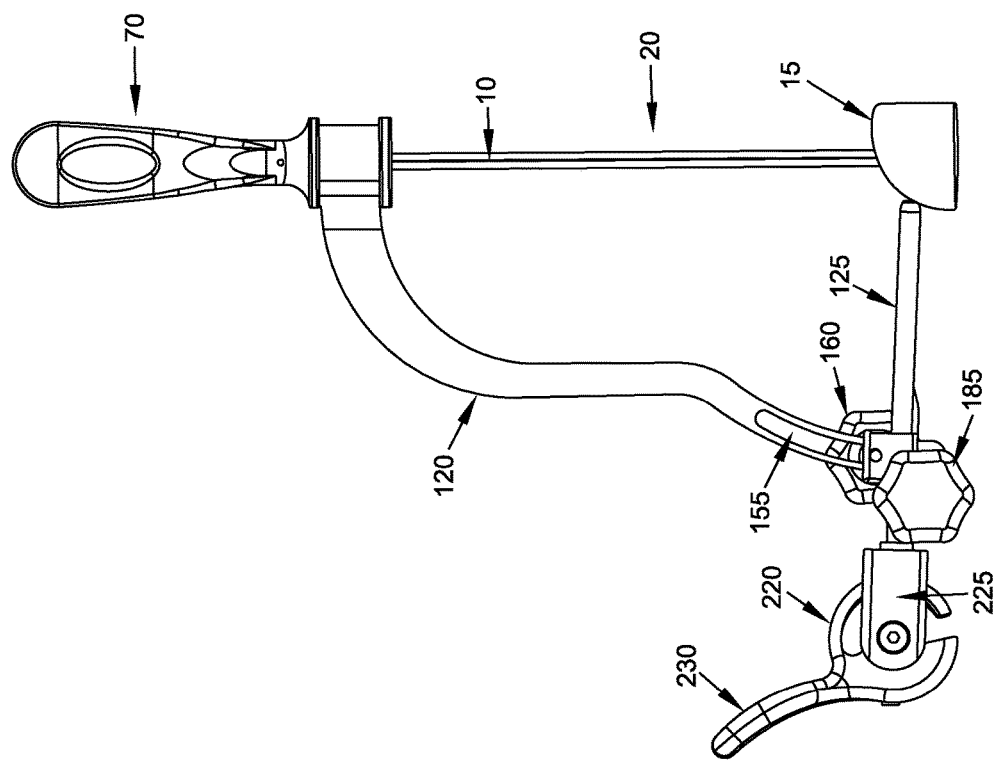

Then, and looking now at FIG. 28, the proximal end of surgical wire 30 is removed from deployment assembly 35. It will be appreciated that the removal of the proximal end of surgical wire 30 does not affect the disposition of the severed distal end of surgical wire 30, which remains securely lodged in bone 15, spanning bone hole 25, and hence extending through loop 235 of the suture 10 loaded onto suture holder 20.

Figure 29:
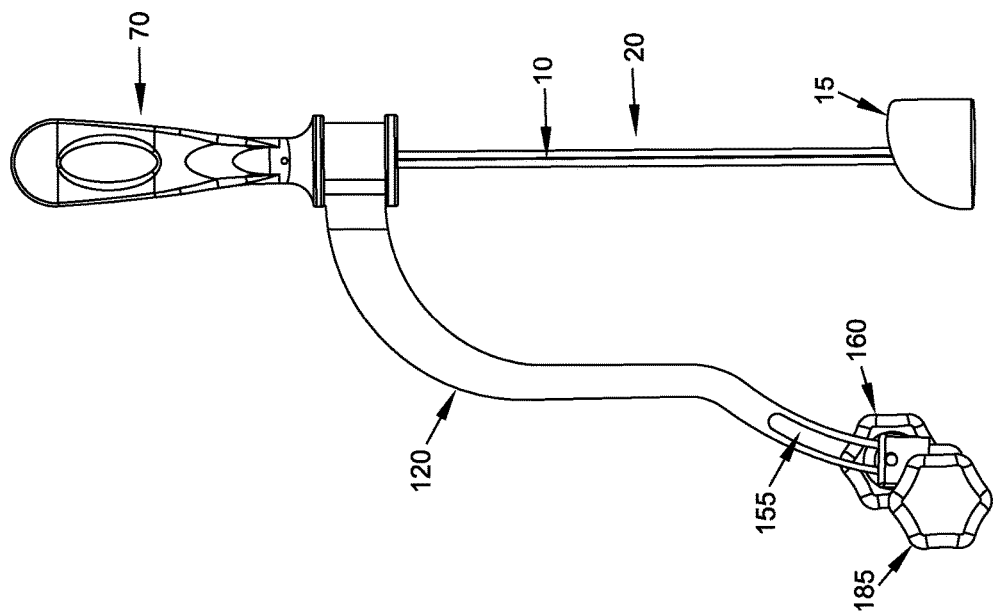

Next, and looking now at FIG. 29, tissue protector 125, collet 130, frame 225 and cam 220/lever 230 are removed (preferably as a unit) from base 115.

Finally, aiming guide 120 and suture holder 20 are removed from the surgical site, leaving the severed distal end of surgical wire 30 spanning bone hole 25, with suture 10 looped around the severed distal end of surgical wire 30, in the manner shown in FIG. 30. Thus, the severed distal end of surgical wire 30 functions as an anchor to attach suture 10 to bone 15. In this respect it will be appreciated that first slot 60, extending between crossbore 55 and the distal tip of suture holder 20, provides a means for withdrawing suture holder 20 from about the severed distal end of surgical wire 30.

Thereafter, the free ends of suture 10 may be used to attach objects (e.g., soft tissue such as a ligament) to bone 15. In this respect it will be appreciated that the severed distal end of surgical wire 30 will provide excellent pull-out strength, due to the fact that its distal and proximal ends are securely embedded in bone on either side of the bone hole, and due to the fact that the load imposed on the suture is applied substantially perpendicular to the longitudinal axis of the severed distal end of the wire. In this respect it will also be appreciated that deployment assembly 35 is configured so that surgical wire 30 can be set at a range of different angles to the longitudinal axis of bone hole 25 (i.e., it can be set at angles other than the substantially 90° angle shown in FIG. 23), such that the disposition of surgical wire 30 in bone 15 can be adjusted so as to maximize anchor pull-out resistance, e.g., by targeting bone of higher bone quality and/or by adjusting the disposition of the surgical wire so as to maintain (as much as possible) the optimal orientation of the surgical wire relative to the "pull line" of the load.

In connection with the foregoing, it should be appreciated that, in order to address differences in anatomy size, or to address variations in bone quality, surgical wire 30 may be formed with its fuse or break joint 100 located closer to sharp point 90 or further away from sharp point 90. By way of example but not limitation, where the patient is of smaller size, or where the soft tissue re-attachment must be conducted in a smaller segment of anatomy (e.g., the hand), fuse or break joint 100 may be located closer to sharp point 90, and where the patient is of larger size, or where the soft tissue re-attachment will impose a heavier load, fuse or break joint 100 may be located farther from sharp point 90. Furthermore, where the host bone is of poorer quality, fuse or break joint 100 may be located farther from sharp point 90 so that a larger length of the severed distal end of surgical wire 30 may be disposed in the patient (the larger length of surgical wire will better carry the load of the suture than a shorter length of surgical wire).

Furthermore, it is also possible to provide surgical wires of greater or lesser diameter, in order to address variations in anatomy size and/or bone quality. By way of example but not limitation, where the tissue re-attachment must be effected in adolescents or in the hand or feet, surgical wires of smaller diameter may be used; and where the tissue re-attachment must be effected in professional athletes or in areas of high ligament load, surgical wires of greater diameter may be used.

In addition, it is also anticipated that surgical wire 30 may be formed out of a variety of materials, e.g., titanium, stainless steel, PEEK, cortical bone, an absorbable material, etc.

In practice, it is intended that a kit of surgical wires be provided, offering a range of different materials, diameters and fuse (break joint) locations.

In the foregoing description, system 5 is described in the context of attaching a suture 10 to a bone 15. However, it should also be appreciated that system 5 may attach multiple sutures to bone 15, e.g., suture holder 20 may be used to support multiple sutures 10 in bone hole 25.

In the foregoing description, system 5 is also described in the context of attaching a suture 10 to a bone 15. However, it should also be appreciated that system 5 may be used to attach other, non-suture types of elongated objects to bone. By way of example but not limitation, system 5 may be used to attach a ligament to bone. In this situation, since such a ligament will likely be larger than suture 10, it will generally be necessary or desirable to "scale up" the size of various aspects of the system, e.g., the size of holder 20, bone hole 25, surgical wire 30, etc. will all generally be increased.

The present invention provides numerous benefits over prior art suture anchors. Among other things, the present invention provides a method and apparatus for attaching an elongated object (e.g., suture) to bone with:
  minimal collateral damage to healthy anatomy resulting from the surgical technique;
  minimal displacement of normal, healthy bone relative to traditional suture anchors;
  minimal size of residual implant;
  superior anchor pull-out resistance;
  confirmation of the successful capture of the suture loop by the surgical wire prior to committing to the deployment of the implant in the bone;
  minimal cost associated with performing the surgical technique; and
  a straight-forward, systematic, easily reproducible technique.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for attaching an elongated object to bone, the apparatus comprising:
  a surgical wire comprising a distal end and a proximal end, and a break joint disposed intermediate the distal end and the proximal end;
  gripping means for selectively gripping the surgical wire distal to the break joint;
  wherein the gripping means comprises a hollow tissue protector having a distal end, a proximal end and a lumen extending therebetween, wherein the hollow tissue protector comprises an internal inclined annular shoulder adjacent to its distal end, and a collet having a distal end, a proximal end and a lumen extending therebetween, wherein the distal end of the collet is compressible, and further wherein the collet is disposed within the tissue protector such that distal movement of the collet causes the collet to engage the internal inclined annular shoulder of the hollow tissue protector and become compressed;

an elongated object holder releasably connected to the tissue protector; and wherein the elongated object holder comprises a distal end and a proximal end, a crossbore extending through the distal end of the elongated object holder, and a slot extending between the crossbore and the distal tip of the elongated object holder.

2. Apparatus according to claim 1 wherein the surgical wire further comprises a sharp distal point.

3. Apparatus according to claim 1 wherein the break joint is formed by appropriately thinning the diameter of the surgical wire at the break joint.

4. Apparatus according to claim 3 wherein the break joint comprises a peripheral surface groove extending into the surgical wire.

5. Apparatus according to claim 1 wherein the break joint is engineered to maintain the structural integrity of the surgical wire at a level of torque below a pre-determined level, and to break upon delivery of a level of torque above that pre-determined level.

6. Apparatus according to claim 5 wherein the pre-determined level of torque is above that needed to drill the surgical wire into bone.

7. Apparatus according to claim 1 wherein the gripping means is disposed over the surgical wire, such that the collet grips a surgical wire disposed therein when the collet is compressed.

8. Apparatus according to claim 1 further comprising a cam follower disposed on the collet, and a cam connected to the tissue protector, wherein movement of the cam follower and the cam relative to one another causes movement of the collet relative to the tissue protector.

9. Apparatus according to claim 1 wherein the distal end of the surgical wire has a diameter which is less than the diameter of the crossbore and the diameter of the slot.

10. Apparatus according to claim 1 wherein the elongated object holder comprises a seat for holding a loop of the elongated object transverse to the crossbore.

11. Apparatus according to claim 10 wherein the seat holds the loop of the elongated object transverse to the crossbore at a location distal to the crossbore.

12. Apparatus according to claim 10 wherein the loop of suture extends across the slot.

13. Apparatus according to claim 10 wherein the seat comprises a second slot extending to the distal tip of the elongated object holder.

14. Apparatus according to claim 1 wherein the tissue protector comprises a first longitudinal axis, the elongated object holder comprises a second longitudinal axis, and further wherein the elongated object holder is releasably connected to the tissue protector so that the angle between the first longitudinal axis of the elongated object holder and the second longitudinal axis of the tissue protector is adjustable.

15. Apparatus according to claim 14 wherein the tissue protector is connected to the elongated object holder by an adjustable guide.

16. Apparatus according to claim 14 wherein the adjustable guide is configured to connect the elongated object holder to the tissue protector so that the lumen of the tissue protector is coaxial with the crossbore in the elongated object holder.

17. Apparatus according to claim 1 wherein the elongated object is suture.

18. Apparatus according to claim 1 wherein the elongated object is selected from the group consisting of a ligament, a tendon and a muscle.

19. Apparatus according to claim 1 comprising a kit of surgical wires, wherein the surgical wires vary from one another in at least one of material composition, wire diameter, break joint location, and the pre-determined level of torque required to break the wire.

* * * * *